United States Patent [19]

Ross et al.

[11] Patent Number: 4,581,464

[45] Date of Patent: Apr. 8, 1986

[54] PREPARATION OF ALKENYL SUCCINIC ANHYDRIDES

[75] Inventors: Victor L. Ross, Bridgeton; Robert G. Schultz, St. Louis, both of Mo.

[73] Assignee: Monsanto Company, St. Louis, Mo.

[21] Appl. No.: 685,423

[22] Filed: Dec. 24, 1984

[51] Int. Cl.$^4$ ............................................. C07D 307/60
[52] U.S. Cl. ..................................... 549/255; 549/233
[58] Field of Search ................................ 549/255, 233

[56] References Cited

U.S. PATENT DOCUMENTS 3,202,679  8/1965  Andrewsen et al. ................ 549/255
3,412,111  11/1968 Irwin et al. .......................... 549/255
3,819,660  6/1974  Cahill et al. ......................... 549/255
4,255,340  3/1981  Powell ................................. 549/255
4,396,774  8/1983  Schaffhausen ...................... 549/255

Primary Examiner—Henry R. Jiles
Assistant Examiner—Bernard I. Dentz
Attorney, Agent, or Firm—R. C. Griesbauer; J. C. Logomasini; A. H. Cole

[57] ABSTRACT

A process for producing alkenyl succinic anhydrides by the reaction of an olefin with maleic anhydride in the presence of alkyl succinic anhydride is provided. The alkenyl succinic anhydrides are valuable precursors for the preparation of alkyl succinic anhydrides.

20 Claims, No Drawings

PREPARATION OF ALKENYL SUCCINIC ANHYDRIDES

This invention relates to a process for producing an alkenyl succinic anhydride by reacting an olefin with maleic anhydride. More particularly this invention relates to production of alkenyl succinic anhydrides by the reaction of an olefin with maleic anhydride in the presence of alkyl succinic anhydride.

BACKGROUND OF THE INVENTION

Alkenyl succinic anhydrides have been prepared by the addition reaction of olefins and maleic anhydride. Generally, the olefin is used in molar excess, for example from about 1.5 to about 5.0 moles of olefin per mole of maleic anhydride to obtain an effective addition reaction. The reaction can be conducted by heating the reactants at a temperature in the range of about 120° to about 250° C. or more for a period of time of from about 0.5 hour to about 24 hours or more. Preferably, the reaction is conducted at a temperature of 165° to 225° C. for a period of 2 to 8 hours.

Various processes have been developed to improve the efficiency of the addition reaction of an olefin and maleic anhydride. U.S. Pat. No. 3,202,679 discloses a process under which the olefin/maleic anhydride addition reaction is conducted under conditions to convert maleic acid impurity in the reaction system to fumaric acid. U.S. Pat. No. 3,412,111 discloses a process employing minor amounts of a hydroxy aromatic or an amino aromatic compound to reduce polymer formation during the addition reaction. U.S. Pat. No. 3,819,660 discloses the use of a catalytic amount of p-alkylbenzene sulfonic acid and 1-3 weight parts of acetic anhydride per part of the sulfonic acid to suppress tar formation during the reaction of 168 to 800 M.W. alkene with maleic anhydride. U.S. Pat. No. 4,255,340 discloses a process for preparing alkenyl succinic anhydride by the addition reaction of an olefin and maleic anhydride in the presence of a catalytic amount brominated hydroxy compound. U.S. Pat. No. 4,396,774 discloses a process for the production of alkenyl succinic anhydrides by the addition reaction of olefin and maleic anhydride in the presence of a catalytic amount of an alkyl aluminum halide.

The alkenyl succinic anhydride and derivatives thereof are useful as additives for fuels, lubricating oil compositions, curing agents for epoxy resins, plasticizers, surfactants etc. Alkenyl succinic anhydrides wherein the alkenyl substituent has from about 6 to 18 carbon atoms are of value as a raw material for the production of $C_6$-$C_{18}$ alkyl diperoxy succinic acid, i.e. $C_6$-$C_{18}$ alkyl substituted butanediperoxoic acid, an effective bleaching agent. See U.S. Pat. No. 4,482,349 issued Nov. 13, 1984 to James M. Mayer.

It has been found that the prior methods of preparing alkenyl succinic anhydrides suitable as precursors for the preparation of $C_6$-$C_{18}$ alkyl succinic anhydride by catalytic hydrogenation, is initially a two phase liquid reaction system. The two phase liquid reaction system suffers the disadvantage of prolonged reaction times, excessive use of energy to maintain the reactants in intimate contact to effect reaction and the formation of undesired polymerization by-products. It has been found that these disadvantages can be overcome by the process of conducting the reaction of a $C_6$-$C_{18}$ alkene with maleic anhydride in the presence of sufficient amount of a $C_6$-$C_{18}$ alkyl succinic anhydride to maintain the reactants in a single liquid phase.

SUMMARY OF THE INVENTION

In accordance with the invention, alkenyl succinic anhydrides are prepared by a process which comprises reacting a $C_6$-$C_{18}$ monoolefin with maleic anhydride in the presence of an effective amount of a $C_6$-$C_{18}$ alkyl succinic anhydride to form a single phase liquid reaction medium.

DETAILED DESCRIPTION OF THE INVENTION

The alkenyl succinic anhydrides are particularly useful as intermediates for the preparation of alkyl succinic anhydrides by the catalytic hydrogenation of the alkenyl succinic anhydrides.

It has been found that effective amounts of a $C_6$-$C_{18}$ alkyl succinic anhydride (ASA) in the "ENE" reaction mixture of a $C_6$-$C_{18}$ alpha monoolefin and maleic anhydride (MAN) provides a single liquid phase reaction medium which accelerates the initial rate of reaction and reduces the amount of interreaction of the alkenyl succinic anhydride product (alkenyl SA) with the olefinic reactants to form undesired by-products.

The amount of the ASA employed in accordance with this invention can vary over a wide range. It is particularly advantageous to employ a sufficient amount of ASA so that at the desired reaction conditions a single liquid phase reaction medium of monoolefin and maleic anhydride reactants is formed whereby the desired ratio of said reactants is uniform throughout. It is advantageous to conduct the ENE reaction with a molar ratio of from about 0.5 to about 5 moles of monoolefin per mole of MAN, preferably about 1.5 to 2.5 moles of monoolefin per mole of MAN.

The determination of the effective amount of ASA to be employed in accordance with this invention can be readily ascertained by routine evaluation as more fully described hereinafter. Generally the amount of ASA employed is about 22 percent or more by weight of ASA based on the combined weight of the ENE reaction mixture employing a molar ratio of 2 moles of 1-decene per mole of MAN. Although much greater amounts of ASA can be employed, the advantages are offset by reduced through-put of product in view of excessive dilution.

The reaction can be conducted at temperatures in the range from about 120° C. to about 250° C. A preferred reaction temperature is from about 150° C. to about 225° C., particularly preferred is the range from 180° C.-210° C. It is advantageous to employ a temperature nearer the lower end of the range and to terminate the reaction prior to completion of the reaction so that the substantial amounts of alkenyl SA which are produced do not form by-products from interreaction with the olefinic materials. In this manner the presence of the ASA promotes the initial rate of reaction of the alpha olefin and MAN and the unreacted olefin and MAN can be separated from the reaction mixture and recycled.

It is advantageous to employ a pressure reaction vessel equipped with a stirrer for conducting the reaction under autogenous pressure.

Various reaction modifiers, such as catalyst to promote the ENE reaction or suppress tar formation and other materials and techniques to reduce by-product formation known in the art can be used in the process of this invention. See for example U.S. Pat. Nos. 3,412,111;

3,819,660; 4,255,340 and 4,396,774 the disclosures of which are incorporated herein by reference.

The alkenyl succinic anhydrides prepared in accordance with this invention are particularly useful for the preparation of the corresponding alkyl succinic anhydride via conventional catalytic hydrogenation techniques. The alkyl succinic anhydride in turn is the precursor for the preparation of alkyl substituted butanediperoxoic acid obtained by peroxidation of the ASA.

The olefin reactant which can be used in this process is a $C_6$ to $C_{18}$ alpha monoolefin or mixtures thereof. Preferred alpha monoolefins are olefins of 8 to 12 carbon atoms or mixtures thereof.

The novel process of this invention is based on the use of $C_6$–$C_{18}$ alkyl succinic anhydride in the ENE reaction mixture to provide a single liquid phase reaction medium. Upon termination of the reaction the unreacted monoolefin and MAN can be separated from the reaction mixture by distillation and recycled. The alkenyl SA product and the alkyl SA can be separated by distillation. Alternatively, and preferably, the mixture can be passed to a hydrogenation reactor for catalytic hydrogenation using conventional techniques. In this manner the alkenyl succinic anhydride in mixture with alkyl succinic anhydride is hydrogenated to produce alkyl succinic anhydride, separation of the alkenyl succinic anhydride from the reaction medium is avoided, and suitable alkyl succinic anhydride product is obtained as precursor for alkyl substituted-butanediperoxoic acid.

This invention is further illustrated by, but not limited to, the following examples wherein all parts and percentages are by weight, unless otherwise indicated.

EXAMPLE I

This Example demonstrates the nature of the two liquid phase ENE reaction in the absence of a suitable solvent.

A reaction mixture was prepared using a 2:1 molar ratio of 1-decene to maleic anhydride.

To a reaction vessel equipped with a stirrer was charged 70 parts 1-decene, 24.5 parts maleic anhydride and 0.25 part hydroquinone polymerization inhibitor. The vessel was sealed and heat was applied with stirring. After about 45 minutes the temperature of the reaction mixture had reached 175°–180° C. Stirring was stopped and the reaction mixture was allowed to separate into two liquid layers. Each layer was sampled and analyzed by gas-liquid chromatography. It was found that the upper layer was 1-decene rich and contained 97.97 mole percent 1-decene, 1.47 mole percent MAN and 0.56 mole percent decenyl SA and that the lower layer was MAN rich and contained 93.04 mole percent MAN, 4.53 mole percent 1-decene and 2.43 mole percent decenyl SA.

This analysis shows that the actual molar ratios present in the two layers differ widely from the described molar ratio of 2 moles olefin per mole of MAN. Although the ENE reaction is occurring in this system, it is inefficient due to the actual molar ratio within the two liquid phases of the reaction mixture. In the 1-decene rich layer, insufficient MAN is present for reaction to be efficient and in the MAN rich layer so little decene-1 is present that sequential reactions of MAN with the decenyl SA product are promoted with the excessive production of by-products of higher molecular weight.

EXAMPLE 2

This example shows the advantages of conducting the ENE reaction in the presence of an effective amount of alkyl succinic anhydride.

Three runs were conducted using the same ratios of 1-decene, MAN and hydroquinone polymerization inhibitor as in Example 1.

Run 1 was conducted with 17% by weight decyl SA based on the total reaction mixture.

Run 2 was conducted with 24.4% by weight decyl SA based on the total reaction mixture.

Run 3 was conducted with 44.0% by weight decyl SA based on the total reaction mixture.

Each run was conducted in a stirred sealed reactor and held at 105° C. overnight prior to increasing the temperature to about 160° C. to promote reaction. Run 1 did not contain sufficient decyl SA to provide a single liquid phase upon standing. With sufficient stirring for good contact with the reactants Run 1 was used for comparison to show advantages achieved by a single liquid phase reaction medium, Runs 2 and 3, which were completely homogeneous and did not separate upon standing. Each run was conducted at about 160° C. for 7 hours. Samples of the reaction mixture were analyzed by gas liquid chromatography. The GLC analysis was normalized to remove the decyl SA content to show the production of decenyl SA in the 3 runs. The weight percent of decenyl SA of Run 2 was 220% of that for the control, Run 1, and that of Run 3 was 187% compared to the control. The improvement in product yield of Run 2 demonstrates the unexpected advantages of conducting the ENE reaction in the presence of an effective amount of alkyl SA. The results of Run 3 further demonstrate that although improved yields are obtained, the advantage of improved yield diminishes with excessive amounts of alkyl SA in the reaction mixture.

EXAMPLE 3

This example shows the unexpected advantages of the properties of ASA to provide a single liquid phase reaction medium for the ENE reaction where compared to conventional solvents.

An ENE reaction mixture was prepared containing 2 moles of 1-decene per mole of MAN and 26.3 percent by weight of mixed xylenes solvent. This mixture was charged to a reaction vessel equipped with a stirrer. The reaction vessel was sealed and heated to 120° C. with stirring. The stirrer was stopped and the reaction mixture formed two layers upon standing. Additional amounts of solvent were added with stirring until the reaction mixture was homogeneous and did not separate upon standing. A total of 47.3 percent by weight of xylenes was required to attain a homogeneous reaction medium at 120° C. which is approximately twice the amount of decyl SA employed in Example 2, Run 2, at 105° C.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A method of preparing alkenyl succinic anhydride which comprises reacting $C_6$-$C_{18}$ monoolefin with maleic anhydride in the presence of an effective amount of $C_6$-$C_{18}$ alkyl succinic anhydride to form a single phase liquid reaction medium.

2. The method of claim 1 wherein the reaction is conducted at a temperature in the range from about 120° C. to 250° C.

3. The method of claim 1 wherein the reaction is conducted with about 0.5 to about 5.0 moles of monoolefin per mole of maleic anhydride.

4. The method of claim 1 wherein the monoolefin is an alpha monoolefin of 8 to 12 carbon atoms or mixtures thereof.

5. The method of claim 4 wherein the reaction is conducted at a temperature in the range from about 150° C. to about 225° C.

6. The method of claim 5 wherein the reaction is conducted with about 2 moles of the monoolefin per mole of maleic anhydride.

7. The method of claim 6 wherein the monoolefin is 1-octene.

8. The method of claim 6 wherein the monoolefin is 1-decene.

9. The method of claim 6 wherein the monoolefin is 1-dodecene.

10. A method of preparing alkenyl succinic anhydride which comprises reacting from 1.5 to 2.5 moles of $C_8$-$C_{12}$ alpha monoolefin with 1 mole of maleic anhydride in the presence of an effective amount of $C_8$-$C_{12}$ alkyl succinic anhydride to form a single phase liquid reaction medium.

11. The method of claim 10 wherein the reaction is conducted at a temperature in the range of about 180° C. to about 210° C.

12. The method of claim 11 wherein the reaction is conducted with about 2 moles of monoolefin per mole of maleic anhydride.

13. The method of claim 11 wherein the monoolefin is 1-octene.

14. The method of claim 11 wherein the monoolefin is 1-decene.

15. The method of claim 11 wherein the monoolefin is 1-dodecene.

16. The method of claim 14 wherein the reaction is conducted with 2 moles of monoolefin per mole of maleic anhydride.

17. The method of claim 14 wherein the alkyl succinic anhydride is present in amount of at least about 20 percent by weight based on the total weight of the reaction mixture.

18. The method of claim 17 wherein the alkyl succinic anhydride is decyl succinic anhydride.

19. A method of preparing decenyl succinic anhydride which comprises reacting 1.5 to 2.5 moles of 1-decene with 1 mole of maleic anhydride at a temperature in the range of about 180° C. to 210° C. in the presence of at least about 20 percent by weight of decyl succinic anhydride.

20. The method of claim 19 wherein the temperature is about 200° C.

* * * * *